United States Patent
Delaria et al.

(10) Patent No.: US 6,294,648 B1
(45) Date of Patent: Sep. 25, 2001

(54) PROTEIN HAVING PROTEINASE INHIBITOR ACTIVITY

(75) Inventors: Kathy Delaria, Walnut Creek; Steve Roczniak, Lafayette; Christopher Davies, Walnut Creek, all of CA (US)

(73) Assignee: Bayer Corporation, Berkeley, CA (US)

( * ) Notice: Subject to any disclaimer, the term of this patent is extended or adjusted under 35 U.S.C. 154(b) by 0 days.

(21) Appl. No.: 09/358,569

(22) Filed: Jul. 20, 1999

(51) Int. Cl.[7] .................................................... A61K 38/00
(52) U.S. Cl. ................................................. 530/300; 514/2
(58) Field of Search ...................................... 435/183, 212, 435/213, 218; 530/300; 514/2

(56) References Cited

U.S. PATENT DOCUMENTS

| | | | |
|---|---|---|---|
| 5,643,758 | * | 7/1997 | Guan et al. ........................... 435/69.7 |
| 5,795,865 | * | 8/1998 | Markland et al. ....................... 514/12 |
| 6,087,473 | * | 7/2000 | Conklin et al. ........................ 530/300 |

FOREIGN PATENT DOCUMENTS

WO 96/20278  *  7/1996  (WO) ............................ C12N/15/15

OTHER PUBLICATIONS

GenBank Accession CAB37635, May 1999.*

* cited by examiner

*Primary Examiner*—Nashaat T. Nashed
*Assistant Examiner*—Christian L Fronda

(57) ABSTRACT

BTL.009 is a novel human serine proteinase inhibitor of the Kunitz family that exhibits greater potency towards neutral serine proteinases, particularly leukocyte elastase, and chymotrypsin than towards trypsin-like proteinases. BTL.009, or variants thereof, may be employed as therapeutics in diseases such as emphysema, idiopathic pulmonary fibrosis, adult respiratory distress syndrome, cystic fibrosis, rheumatoid arthritis, organ failure, and glomerulonephritis in which uncontrolled proteolysis due to neutral serine proteinase activity results in tissue damage.

6 Claims, No Drawings

SEQUENCE LISTING

<160> NUMBER OF SEQ ID NOS: 15

<210> SEQ ID NO: 1
<211> LENGTH: 55
<212> TYPE: PRT
<213> ORGANISM: Artificial Sequence
<220> FEATURE:
<223> OTHER INFORMATION: Description of Artificial Sequence:derived from EST sequence database

<400> SEQUENCE: 1

Lys Gln Asp Val Cys Glu Met Pro Lys Glu Thr Gly Pro Cys Leu Ala
 1               5                  10                  15

Tyr Phe Leu His Trp Trp Tyr Asp Lys Lys Asp Asn Thr Cys Ser Met
             20                  25                  30

Phe Val Tyr Gly Gly Cys Gln Gly Asn Asn Asn Phe Gln Ser Lys
         35                  40                  45

Ala Asn Cys Leu Asn Thr Cys
     50                  55

<210> SEQ ID NO: 2
<211> LENGTH: 58
<212> TYPE: PRT
<213> ORGANISM: Artificial Sequence
<220> FEATURE:
<223> OTHER INFORMATION: Description of Artificial Sequence:Fragment of protein from database containing Kunitz domain

<400> SEQUENCE: 2

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
     50                  55

<210> SEQ ID NO: 3
<211> LENGTH: 55
<212> TYPE: PRT
<213> ORGANISM: Artificial Sequence
<220> FEATURE:
<223> OTHER INFORMATION: Description of Artificial Sequence:Fragment of protein from database containing Kunitz domain

<400> SEQUENCE: 3

Val Arg Glu Val Cys Ser Glu Gln Ala Glu Thr Gly Pro Cys Arg Ala
 1               5                  10                  15

Met Ile Ser Arg Trp Tyr Phe Asp Val Thr Glu Gly Lys Cys Ala Pro
             20                  25                  30

```
Phe Phe Tyr Gly Gly Cys Gly Gly Asn Arg Asn Asn Phe Asp Thr Glu
            35                  40                  45

Glu Tyr Cys Met Ala Val Cys
 50                  55

<210> SEQ ID NO: 4
<211> LENGTH: 58
<212> TYPE: PRT
<213> ORGANISM: Artificial Sequence
<220> FEATURE:
<223> OTHER INFORMATION: Description of Artificial Sequence:Fragment of
      protein from database containing Kunitz domain

<400> SEQUENCE: 4

Glu Thr Asp Ile Cys Lys Leu Pro Lys Asp Glu Gly Thr Cys Arg Asp
 1               5                  10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
            35                  40                  45

Lys Glu Cys Glu Lys Val Cys Ala Pro Val
 50                  55

<210> SEQ ID NO: 5
<211> LENGTH: 58
<212> TYPE: PRT
<213> ORGANISM: Artificial Sequence
<220> FEATURE:
<223> OTHER INFORMATION: Description of Artificial Sequence:Fragment of
      protein from database containing Kunitz domain

<400> SEQUENCE: 5

Met His Ser Phe Cys Ala Phe Lys Ala Asp Asp Gly Pro Cys Lys Ala
 1               5                  10                  15

Ile Met Lys Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55

<210> SEQ ID NO: 6
<211> LENGTH: 55
<212> TYPE: PRT
<213> ORGANISM: Artificial Sequence
<220> FEATURE:
<223> OTHER INFORMATION: Description of Artificial Sequence:Fragment of
      protein from database containing Kunitz domain

<400> SEQUENCE: 6

Lys Pro Asp Arg Cys Phe Leu Glu Glu Asp Pro Gly Ile Cys Arg Gly
 1               5                  10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
            35                  40                  45

Glu Glu Cys Lys Asn Ile Cys
 50                  55

<210> SEQ ID NO: 7
<211> LENGTH: 58
<212> TYPE: PRT
```

```
<213> ORGANISM: Artificial Sequence
<220> FEATURE:
<223> OTHER INFORMATION: Description of Artificial Sequence:Fragment of
      protein from database containing Kunitz domain

<400> SEQUENCE: 7

Gly Pro Ser Trp Cys Leu Thr Pro Ala Asp Arg Gly Leu Cys Arg Ala
 1               5                  10                  15

Asn Glu Asn Arg Phe Tyr Tyr Asn Ser Val Ile Gly Lys Cys Arg Pro
            20                  25                  30

Phe Lys Tyr Ser Gly Cys Gly Gly Asn Glu Asn Asn Phe Thr Ser Lys
        35                  40                  45

Gln Glu Cys Leu Arg Ala Cys Lys Lys Gly
    50                  55

<210> SEQ ID NO: 8
<211> LENGTH: 54
<212> TYPE: PRT
<213> ORGANISM: Artificial Sequence
<220> FEATURE:
<223> OTHER INFORMATION: Description of Artificial Sequence:derived from
      EST sequence database

<400> SEQUENCE: 8

Asp Val Cys Glu Met Pro Lys Glu Thr Gly Pro Cys Leu Ala Tyr Phe
 1               5                  10                  15

Leu His Trp Trp Tyr Asp Lys Lys Asp Asn Thr Cys Ser Met Phe Val
            20                  25                  30

Tyr Gly Gly Cys Gln Gly Asn Asn Asn Asn Phe Gln Ser Lys Ala Asn
        35                  40                  45

Cys Leu Asn Thr Cys Lys
    50

<210> SEQ ID NO: 9
<211> LENGTH: 54
<212> TYPE: PRT
<213> ORGANISM: Artificial Sequence
<220> FEATURE:
<223> OTHER INFORMATION: Description of Artificial Sequence:derived from
      EST sequence database

<400> SEQUENCE: 9

Asp Leu Cys Gln Leu Pro Gln Ala Arg Gly Pro Cys Lys Ala Ala Leu
 1               5                  10                  15

Leu Arg Tyr Phe Tyr Asn Ser Thr Ser Asn Ala Cys Glu Pro Phe Thr
            20                  25                  30

Tyr Gly Gly Cys Gln Gly Asn Asn Asn Asn Phe Glu Thr Thr Glu Met
        35                  40                  45

Cys Leu Arg Ile Cys Glu
    50

<210> SEQ ID NO: 10
<211> LENGTH: 64
<212> TYPE: PRT
<213> ORGANISM: Artificial Sequence
<220> FEATURE:
<223> OTHER INFORMATION: Description of Artificial Sequence:Extension of
      Seq Id 1

<400> SEQUENCE: 10

Asp Leu Lys Gln Asp Val Cys Glu Met Pro Lys Glu Thr Gly Pro Cys
 1               5                  10                  15
```

Leu Ala Tyr Phe Leu His Trp Trp Tyr Asp Lys Lys Asp Asn Thr Cys
            20                  25                  30

Ser Met Phe Val Tyr Gly Gly Cys Gln Gly Asn Asn Asn Phe Gln
            35                  40                  45

Ser Lys Ala Asn Cys Leu Asn Thr Cys Lys Asn Lys Arg Phe Pro Glu
    50                  55                  60

<210> SEQ ID NO: 11
<211> LENGTH: 55
<212> TYPE: PRT
<213> ORGANISM: Artificial Sequence
<220> FEATURE:
<223> OTHER INFORMATION: Description of Artificial Sequence:derived from
      EST database

<400> SEQUENCE: 11

Asp Phe Cys Phe Leu Glu Glu Asp Pro Gly Ile Cys Arg Gly Phe Met
 1               5                  10                  15

Thr Arg Tyr Phe Tyr Asn Asn Gln Ser Lys Gln Cys Glu Gln Phe Lys
            20                  25                  30

Tyr Gly Gly Cys Leu Gly Asn Ser Asn Asn Phe Glu Thr Leu Glu Glu
            35                  40                  45

Cys Arg Asn Thr Cys Glu Asp
    50                  55

<210> SEQ ID NO: 12
<211> LENGTH: 11
<212> TYPE: PRT
<213> ORGANISM: Artificial Sequence
<220> FEATURE:
<223> OTHER INFORMATION: Description of Artificial Sequence:derived from
      EST database

<400> SEQUENCE: 12

Asp Val Cys Glu Met Pro Lys Glu Thr Gly Thr
 1               5                  10

<210> SEQ ID NO: 13
<211> LENGTH: 43
<212> TYPE: PRT
<213> ORGANISM: Artificial Sequence
<220> FEATURE:
<223> OTHER INFORMATION: Description of Artificial Sequence: Artificial
      sequence derived from EST database

<400> SEQUENCE: 13

Leu Ala Tyr Phe Leu His Trp Trp Tyr Asp Lys Lys Asp Asn Thr Cys
 1               5                  10                  15

Ser Met Phe Val Tyr Gly Gly Cys Gln Gly Asn Asn Asn Phe Gln
            20                  25                  30

Ser Lys Ala Asn Cys Leu Asn Thr Cys Lys Asn
            35                  40

<210> SEQ ID NO: 14
<211> LENGTH: 51
<212> TYPE: PRT
<213> ORGANISM: Artificial Sequence
<220> FEATURE:
<223> OTHER INFORMATION: Description of Artificial Sequence:from
      computer database

<400> SEQUENCE: 14

Arg Thr Pro Ser Asp Lys Pro Val Ala His Val Ala Asn Pro Gln Leu
 1               5                  10                  15

-continued

```
Gln Trp Leu Asn Arg Arg Ala Asn Ala Leu Leu Ala Asn Gly Val Glu
                20                  25                  30

Arg Asp Asn Gln Leu Val Val Glu Gly Leu Tyr Leu Ile Tyr Ser Gln
            35                  40                  45

Val Leu Phe
    50

<210> SEQ ID NO: 15
<211> LENGTH: 52
<212> TYPE: PRT
<213> ORGANISM: Artificial Sequence
<220> FEATURE:
<223> OTHER INFORMATION: Description of Artificial Sequence:from
      computer database

<400> SEQUENCE: 15

Arg Ala Pro Phe Lys Lys Ser Trp Ala Tyr Leu Gln Val Ala Lys His
 1               5                  10                  15

Lys Leu Ser Trp Asn Lys Asp Gly Ile Leu His Gly Val Arg Tyr Gln
                20                  25                  30

Asp Gly Asn Leu Val Ile Gln Phe Pro Gly Leu Tyr Phe Ile Ile Cys
            35                  40                  45

Gln Leu Gln Phe
    50
```

PROTEIN HAVING PROTEINASE INHIBITOR ACTIVITY

BACKGROUND OF THE INVENTION

Field

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been identified as a member of the Kunitz serine proteinase inhibitor family and is hereinafter referred to as BTL.009.

Inflammatory Diseases

The inflammatory response after surgeries, trauma and infection involves neutrophil activation and infiltration into the injured tissue. The activated neutrophils release the neutral serine proteinases leukocyte elastase, cathepsin G and proteinase 3, which, if not properly controlled, cause abnormal connective tissue turnover and result in severe damage to healthy tissue (1–3, 81). The uncontrolled proteolysis can lead to a myriad of diseases including emphysema, idiopathic pulmonary fibrosis, adult respiratory distress syndrome, cystic fibrosis, rheumatoid arthritis, organ failure, and glomerulonephritis.

Proteins capable of inhibiting the neutral serine proteinases released by neutrophils can have therapeutic efficacy in treating inflammatory diseases. In patients suffering from hyperdynamic septic shock, plasma levels of the serine proteinase inhibitors antithrombin III, alpha 2-macroglobulin and inter-alpha-trypsin inhibitor, as well as those of various clotting, complement and other plasma factors, are significantly decreased (5). In an experimental endotoxemia model, the reduction in the plasma levels of these factors was considerably diminished by the intravenous injection of a soybean-derived leukocyte elastase and cathepsin G inhibitor, indicating that these neutral proteinases are at least partially responsible for the proteolysis of the plasma factors. In addition, the survival rate in the rat lethal peritonitis model (cecal ligation and puncture-induced septic shock model) was improved by treatment with the second domain of human urinary trypsin inhibitor (2), which has been shown to inhibit leukocyte elastase and cathepsin G (6, 7).

Stimulated neutrophils generate active oxygen species which contribute to inflammatory diseases, necrosis of surrounding tissues, mutagenicity and carcinogenicity (8). The most effective serine protease inhibitors in decreasing $H_2O_2$ formation by TPA-activated neutrophils were chymotrypsin-specific inhibitors (e.g., potato inhibitor-1 and a chymotrypsin-inhibitory fragment of potato inhibitor-2), followed by bifunctional inhibitors recognizing both chymotrypsin and trypsin, and least active was soybean trypsin inhibitor, a predominantly trypsin inhibitor. In addition, cytin, a chymotrypsin- but not trypsin-specific inhibitor, significantly diminished the level of human neutrophil and monocyte activation induced by lipopolysaccharide (9).

Neutrophil chemotaxis also plays an important role in the inflammatory response and, when excessive or persistent, may augment tissue damage (10). Inhibitors of cathepsin G and chymotrypsin suppressed neutrophil chemotaxis to the chemoattractants N-formyl-L-methionyl-L-leucyl-L-phenylalanine (fMLP) and zymosan-activated serum in multiple blind well assays and to fMLP in migration assays under agarose.

IL-1, a proinflammatory cytokine, is secreted from monocytes at inflammatory sites as an inactive precursor. Leukocyte elastase and cathepsin G cleave the IL-1 precursor to form fully active forms of IL-1 (11). Synovial fluid collected from patients with inflammatory polyarthritis and bronchoalveolar lavage fluid from patients with sarcoidosis process the IL-1 precursor into the same active forms as leukocyte elastase and cathepsin G. Control fluids from patients who had no symptoms of inflammatory disease did not exhibit the processing activity. Only lavage fluids that processed precursor IL-1 contain cathepsin G and/or elastase activity.

Synthetic tannin exhibits anti-inflammatory properties in skin diseases. Tannin specifically inhibits leukocyte elastase in an irreversible manner and it is believed that the anti-inflammatory properties of synthetic tannin may at least in part be due to inactivation of elastase (12).

Lung Injury

Many syndromes of lung injury, including emphysema, adult respiratory distress syndrome, cystic fibrosis and idiopathic pulmonary fibrosis, are associated with accumulation of neutrophils within the pulmonary parenchyma. Activated neutrophils have the capacity to produce lung injury by secreting products including proteinases and reactive oxygen species (13). Neutral serine proteinases secreted from activated neutrophils are capable of inducing damage to lung alveolar extracellular matrix (ECM) by directly digesting the matrix and through the activation of latent metalloproteases resident in the matrix (14). Proteinase 3 and leukocyte elastase have been shown to cause significant lung damage and emphysema when administered by tracheal insufflation or injection to hamsters (16, 17).

Inhibitors of neutrophil neutral serine proteinases have been shown to exert potent therapeutic effects on pulmonary emphysema, adult respiratory distress syndrome and other diseases involving tissue degradation. Treatment of hamsters with Eglin c, a neutral serine proteinase inhibitor, completely protected hamsters against leukocyte elastase-induced emphysema (18). Derivatives of 5-methyl-4H-3,1-benzoxazin-4-one, shown to be highly specific inhibitors of leukocyte elastase, efficiently prevented degradation of insoluble elastin by stimulated neutrophils (19). These small molecule inhibitors also significantly suppressed leukocyte induced pulmonary hemorrhage and emphysema in hamsters (19). Alpha 1-proteinase inhibitor and soybean trypsin inhibitor, two leukocyte elastase and cathepsin G inhibitors, were also shown to completely or nearly completely inhibit neutrophil-induced ECM solubilization (13).

However, alpha 1-proteinase inhibitor, the major endogenous serine proteinase inhibitor for neutrophil elastase, is easily inactivated by proteolysis by metalloproteinases present in the injured lung and by oxidation (20, 21). Oxidative inactivation of alpha 1-proteinase has been linked to the pathogenesis of pulmonary emphysema associated with cigarette smoking (22).

Vascular Effects

Injury to the vascular endothelium, such as that occurs during angioplasty, can result in the accumulation of neutrophils and platelets and platelet activation at the site of injury. Platelet accumulation and activation at the injured site can result in abrupt artery closure. Cathepsin G potently induces platelet aggregation, secretion and calcium mobilization by binding to a specific receptor on platelets (23). Leukocyte elastase, though having no platelet agonist activity itself, increases the apparent affinity of cathepsin G binding to platelets and enhances cathepsin G-induced platelet activation. Thrombospondin 1, which inactivates cathepsin G by binding near the enzyme's active site, protected fibronectin from cleavage by cathepsin G and blocked cathepsin G-mediated platelet aggregation (24).

Endothelin-1 (ET-1) is potent vasoconstrictor peptide secreted by endothelial cells. Marked ET-1 degradation is observed in the presence of activated neutrophils. ET-1 inactivation could play a role in acute inflammatory reactions where neutrophils adhere to the vascular endothelial cells. Soybean trypsin inhibitor abolishes ET-1 degradation almost completely, suggesting a role of cathepsin G in ET-1 hydrolysis (25). Among the purified leukocyte enzymes tested, cathepsin G hydrolyzed ET-1 at the highest rate.

Cathepsin G converts angiotensinogen and angiotensin I to angiotensin II (26, 27). The neutrophil-angiotensin system does not require renin or converting enzyme and may function as a mobile effector pathway which modulates tissue blood flow and/or vascular permeability.

Proteinase Inhibitor Structure and Specificity

Cathepsin G, leukocyte elastase and proteinase 3 are neutral serine proteinases that exist primarily in azurophilic granules of neutrophils. Elastase has a preference for hydrophobic (e.g., neutral) residues at the P1 site such as valine, alanine, isoleucine and leucine (28, 29). (The reactive-site sequence of proteinase inhibitors and substrates are written as . . . -P3-P2-P1-P'1-P'2-P'3- . . . , where-P1-P'1-denotes the reactive site). Cathepsin G has a similar preference for large hydrophobic residues (i.e., phenylalanine, leucine) and basic residues (lysine, arginine) and exhibits dual and equal trypsin- and chymotrypsin-like specificities (30). Proteinase 3 prefers small aliphatic amino acids such as alanine, serine and valine at the P1 site (15, 31). The P3-S3 interaction during human leukocyte elastase hydrolysis of peptide substrates has also been determined to be important (32). (S3 refers to the residue on the inhibited proteinase that interacts with the P3 residue on the inhibitor.)

Kunitz Inhibitors

Protein inhibitors of serine proteinases can be grouped into several families, including the Kunitz, serpin, Kazal, and mucous protein inhibitor families, based on conserved structural features. Members of each family exhibit greatly varied binding specificities, and members of different families can have similar inhibitory profiles. The binding specificities of the proteinase inhibitors are determined by the residue at the P1 position as well as other residues that lie at the interface between the inhibitor and the bound target proteinase. The P1 residue in Kunitz domain proteins lies immediately C-terminal to the conserved second cysteine (position 15; aprotinin numbering).

All members of the Kunitz domain protein family have the same number (six) and spacing of cysteine residues. The precise bonding of cysteine residues to form the three intrachain disulfide bonds is known and invariant for all previously known Kunitz members (33).

Members of the Kunitz domain protein family function as inhibitors of serine proteases. Each inhibitor has a unique inhibition specificity profile towards the serine proteases. However, inhibitors with a basic residue (i.e., arginine or lysine) immediately following the second cysteine residue tend to have greater potencies towards proteases that cleave proteins at basic residues. In addition, mutation of the lysine residue at this position in aprotinin to a valine resulted in a dramatic increase in the protein's potency towards neutrophil elastase, a protease that typically cleaves proteins at residues with small neutral aliphatic side chains (34).

The serine protease inhibitory activities of the Kunitz domain proteins has led to their evaluation as potential therapeutics in a number of disease indications. For example, aprotinin is a potent inhibitor of proteases involved in the blood clotting cascade and is used clinically to reduce bleeding during open heart surgery (35). Human placental bikunin is a potent inhibitor of plasmin, which has been implicated in facilitating metastasis and tumor growth (36). Other disease indications in which serine proteases are believed to play a significant pathological role and the Kunitz domain proteins may therefore be effective therapeutics include traumatic brain injury and stroke (37, 38), cystic fibrosis (39, 40), emphysema (41), arthritis and anemia (42) and non-insulin dependent diabetes (43).

Kunitz domains that exist within larger proteins have been shown to retain their functional activities when produced as single domains (44). Kunitz-type inhibitors have been described in the patent literature (85).

Serine proteinase inhibitors of the Kunitz family typically exhibit significantly tighter binding to trypsin and chymotrypsin, two proteases with relatively strict P1 specificities (trypsin=arginine, lysine; chymotrypsin=tyrosine, phenylalanine, tryptophan) but with few restrictions at other P and P' positions, than to the three neutral proteinases secreted by neutrophils. For example, aprotinin is a potent inhibitor of trypsin (Ki=0.02 nM) and chymotrypsin (Ki=1.3 nM) but does not inhibit leukocyte elastase (44). Similarly, placental bikunin inhibits trypsin (Ki=0.01 nM) and chymotrypsin (Ki=0.48 nM) but not leukocyte elastase (44). Tissue factor pathway inhibitor (TFPI), another member of the Kunitz family, inhibits trypsin (0.1 nM) and chymotrypsin (Ki=0.75 nM) but is a weak inhibitor of leukocyte elastase (Ki=400 nM) and cathepsin G (Ki=100–200 nM) (45, 46). In addition, these Kunitz family members exhibit potent inhibitory activity towards serine proteinases having trypsin-like substrate specificity involved in both coagulation and fibrinolysis (44–47). Elastase and cathepsin G have been reported to proteolytically cleave and inactivate TFPI (4, 46).

Human inter-alpha-trypsin inhibitor (I alpha I), a plasma Kunitz family proteinase inhibitor, is a potent inhibitor of trypsin (Ki=0.078 nM) and chymotrypsin (1. 1 nM) but exhibits somewhat lesser activity against cathepsin G (Ki=18 nM) and leukocyte elastase (Ki=61 nM) (6). Similarly, a Kunitz-type inhibitor purified from Japanese horseshoe crab (Tachypleus tridentatus) hemocytes potently inhibited trypsin (Ki=0.46 nM) and chymotrypsin (Ki=5.5 nM), but was somewhat less active towards leukocyte elastase (Ki=72 nM) (48).

Soybean trypsin inhibitor (STI) is a potent Kunitz family inhibitor of tryspin but a significantly weaker inhibitor of chymotrypsin (Ki(1)=1000 nM; Ki(2)=300 nM) (49). STI has been reported to exhibit similar inhibitory activity towards chymotrypsin and leukocyte elastase (25). On the other hand, a serine protease inhibitor from larvae of parasitic nematode Anisakis simplex that has 96% amino acid identity to soybean trypsin inhibitor was reported to inhibit trypsin and elastase but not chymotrypsin (50). In addition, a Kunitz-type inhibitor purified from potato tubers (Solanum tuberosum L) was reported to be an effective inhibitor of trypsin, leukocyte elastase, and chymotrypsin (51).

Non-Kunitz Proteinase Inhibitors

Numerous serine proteinase inhibitors from families other than that of the Kunitz family have been reported to inhibit neutral serine proteinases, including those secreted by activated neutrophils. Alpha-1-proteinase and alpha-2-macroglobulin, members of the serpin proteinase inhibitor family, inhibit elastase, cathepsin G and proteinase 3 (15, 52–55). Alpha-1-proteinase has been described as the major serum inhibitor of elastase and cathepsin G (54). Alpha-1-antichymotrypsin, another serpin family proteinase inhibitor, inhibits cathepsin G (53, 56, 55) but not proteinase 3 (15), and has been described as another physiological cathepsin G inhibitor (53). Monocyte/neutrophil elastase inhibitor, also a serpin family inhibitor, inhibits elastase and proteinase 3 (57). Antileukoproteinase (SLPI) and elafin, members of the mucous proteinase inhibitor family, inhibit elastase (Ki=0.6 mM) (58, 59) but not proteinase 3 (15) and cathepsin G (58). Eglin C, a member of the potato inhibitor 1 family from leech Hirudo medicinalis, inhibits leukocyte elastase (Ki=0.37 nM) and cathepsin G (Ki~0.1 nM) (60–62) but only weakly inhibits proteinase 3 (15).

The largest EST (AI023486) is also the most 5' sequenced EST in the transcript. All other EST's listed are contained within AI023486. The Genbank-derived automatically generated annotation, shows that AI023486 has similarity to SW:IBPC_BOVIN P00976 COLOSTRUM TRYPSIN INHIBITOR (which happens to contain a Kunitz domain, although this is not mentioned in the annotation).

When translated and searched against the Genpept peptide database, this EST sequence was found to have a highest match of 48% to "trypsin inhibitor" (as shown below, in the reverse ORF), confirming its novelty.

```
>gi|208050 (M31335) trypsin inhibitor [artificial sequence] Length = 68
  Score = 171, Expect = 0.0, P = 0.0
  Identities = 26/54 (48%), Positives = 36/54 (66%), Start Frame = -3

Query:    DVCEMPKETGPCLAYFLHWWYDKKDNTCSMFVYGGCQGNNNNFQSKANCLNTCK
          D+C++P+  GPC A L ++Y+   N C  F YGGCQGNNNNF++   CL C+
Sbjct:    DLCQLPQARGPCKAALLRYFYNSTSNACEPFTYGGCQGNNNNFETTEMCLRICE
(Query is SEQ ID NO:8; Sbjct is SEQ ID NO:9.)
```

SUMMARY OF THE INVENTION

A potential coding sequence containing a putative Kunitz domain sequence was identified by searching a computer database of EST sequence information. There are many Kunitz domain-containing proteins already known, and many of these are represented in the EST (Expressed Sequence Tag) DNA databases at NCBI (National Center for Biotechnology Information). A homology search in the EST database, using a single Kunitz protein query, will yield many alignments to Kunitz domain-containing EST's. Without further data reduction, it is not possible to tell which of these alignments are versus EST's corresponding to other known Kunitz proteins, and which are novel, regardless of their annotation in the EST database.

The BTL.009 protein was found by searching in a reduced data set. This data set is a version of the Genbank Unigene clustered EST database which was generated by using a DNA sequence assembly algorithm to assemble each cluster in the Unigene database, thus creating a smaller number of consensus sequences. The first new Kunitz domain protein was discovered in this assembled database by using the database search algorithm TBLASTN, with Rat tissue factor pathway inhibitor precursor protein sequence (Genbank ID numbers: gi220917|, accession# d1002199) as a query.

The significant alignment generated was thus:

The putative protein coding sequence of the EST-derived Kunitz protein, from the end of the clone to the first stop codon is thus: DLKQDVCEMPKETGPCLAYFLHWWYD-KKDNTCSMFVYGGCQGNNNNFQSKAN-CLNTCKNKRFPE (SEQ ID NO:10). There is no methionine (start) codon in the EST's that is in frame and 5' to the start of the Kunitz domain homology, implying that further sequencing in these EST's and ultimately of the full length transcript will extend the protein coding sequence in the 5' direction.

The present invention encompasses a newly identified human protein, herein called BTL.009, which has been identified as a member of the Kunitz family of proteinase inhibitors based on the presence of the conserved six cysteines observed in all members of this family. BTL.009 was found to inhibit preferentially chymotrypsin-like proteases over trypsin-like proteases. BTL.009 is also an elastase inhibitor.

The instant invention encompasses the use of BTL.009 for preventing neutrophil and monocyte activation and formation of active oxygen species during the oxidative burst of stimulated granulocytes. The current invention further encompasses the use of BTL.009 for reducing platelet activation and blood coagulation. The invention may also be useful in a method for the prophylactic or therapeutic treatment of patients undergoing angioplasty. The instant invention also encompasses pharmaceutical compositions

```
>392421746.FastaFile.screen.Contig1
                     392421746 Assembled_Cluster.34861 @ 34861
         ID Hs.121084 TITLE ESTs SCOUNT 4             Length = 490
  Score = 125 (44.0 bits), Expect = 2.9e-07, P = 2.9e-07
  Identities = 19/55 (34%), Positives = 32/55 (58%), Frame = -1

Query: 122 DFCFLEEDPGICRGFMTRYFYNNQSKQCEQFKYGGCLGNSNNFETLEECRNTCED 176
           D C + ++ G    +    ++Y+ +   C  F YGGC GN+NNF++   C NTC++
Sbjct: 487 DVCEMPKETGT*LAYFLHWWYDKKDNTCSMFVYGGCQGNNNNFQSKANCLNTCKN 323
(Query is SEQ ID NO:11; Sbjct is SEQ ID NOs:12 and 13.)
```

As can be seen from the TITLE annotation of "EST's" for this cluster, no definite function had been attributed to it at that time, making it a candidate for a novel kunitz protein. EST's belonging in this cluster (and sharing identity with the 4 cluster EST's) are: AI023486 (Genbank accession numbers), AA725746, AI003865, AA759074, AA860417, H56776, AA928202.

containing BTL.009 that are useful for the treatment of inflammatory diseases and diseases involving lung and vascular injury.

In accordance with one aspect of the present invention, there are provided novel mature polypeptides comprising the amino acid sequence given in SEQ ID NO:1 as well as biologically active and diagnostically or therapeutically useful fragments, analogues and derivatives thereof In accordance with another aspect of the present invention, there are provided isolated nucleic acid molecules encoding the polypeptides of the present invention, including mRNAs, DNAs, cDNAs, genomic DNA, as well as antisense analogs thereof and biologically active and diagnostically or therapeutically useful fragments thereof.

In accordance with still another aspect of the present invention, there are provided processes for producing such polypeptides by recombinant techniques through the use of recombinant vectors. As a further aspect of the present invention, there are provided recombinant prokaryotic and/or eukaryotic host cells comprising a nucleic acid sequence encoding a polypeptide of the present invention.

In accordance with a further aspect of the present invention, there is provided a process for utilizing such polypeptides, or polynucleotides encoding such polypeptides, for therapeutic purposes, for example, preventing neutrophil and monocyte activation and formation of active oxygen species during the oxidative burst of stimulated granulocytes; or for reducing platelet activation and blood coagulation, or for the treatment of inflammatory diseases and diseases involving lung and vascular injury.

In accordance with another aspect of the present invention, there are provided nucleic acid probes comprising nucleic acid molecules of sufficient length to specifically hybridize to a polynucleotide encoding a polypeptide of the present invention.

In accordance with yet another aspect of the present invention, there are provided diagnostic assays for detecting diseases or susceptibility to diseases related to mutations in a nucleic acid sequence of the present invention and for detecting over-expression of the polypeptides encoded by such sequences.

In accordance with another aspect of the present invention, there is provided a process involving expression of such polypeptides, or polynucleotides encoding such polypeptides, for purposes of gene therapy. As used herein, gene therapy is defined as the process of providing for the expression of nucleic acid sequences of exogenous origin in an individual for the treatment of a disease condition within that individual.

DETAILED DESCRIPTION OF THE INVENTION

The polypeptides of the present invention comprise polypeptides having the deduced amino acid sequence given by SEQ ID NO:1. The polypeptides of the present invention may include additional amino acid sequences appended to the N- or C-terminal of the peptides having the deduced amino acid sequence given by SEQ ID NO:1. The polypeptides of the present invention may be recombinant polypeptides, natural polypeptides, or synthetic polypeptides, preferably recombinant polypeptides. As used herein, "protein" is synonymous with "polypeptide."

The present invention further includes a polypeptide which shares at least a 60%, more preferably at least an 80%, still more preferably a 90%, or most preferably at least a 95% sequence identity over at least 20, more preferably at least 30, still more preferably at least 40, or most preferably at least 50 residues with SEQ ID NO:1. (Such polypeptides may be herein referred to as "polypeptides of the present invention".)

Such a polypeptide as described above may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethyleneglycol), or (iv) one in which additional amino acids are fused to the mature polypeptide, such as a leader or secretory sequence or a sequence which is employed for purification of the mature polypeptide or a proprotein sequence or mature protein sequence beyond the Kunitz domain, or (v) one in which one or more amino acids are deleted from or inserted into the sequence of the polypeptide. Combinations of the above-described types of variations in the peptide sequence are within the scope of the invention. Such polypeptides are deemed to be within the scope of those skilled in the art from the teachings herein.

The polypeptide of the present invention may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (63–66)

The polypeptides and polynucleotides of the present invention are preferably provided in an isolated form, and preferably are purified to homogeneity. The term "isolated" means that the material is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

As known in the art "similarity" between two polypeptides is determined by comparing the amino acid sequence and its conserved amino acid substitutes of one polypeptide to the sequence of a second polypeptide. Such conservative substitutions include those described by Dayhoff (67) and by Argos (68). For example, amino acids belonging to one of the following groups represent conservative changes:

ala, pro, gly, gln, asn, ser, thr;

cys, ser, tyr, thr;

val, ile, leu, met, ala, phe;

lys, arg, his;

phe, tyr, trp, his; and asp, glu.

(Note that these grouping are examples; other groupings may represent more relevant choices.)

"Similarity" or "identity" refers to sequence conservation, or "homology", between two or more peptides or two or more nucleic acid molecules, normally expressed in terms of percentages. When a position in the compared sequences is occupied by the same base or amino acid ("residue"), then the molecules are identical at that position. When a position in two compared peptide sequences is occupied by an amino acid with similar physical properties (a conservative substitution as determined by a given scoring matrix; similarity is thus dependent on the scoring matrix chosen), then the molecules are similar at that position. The percent identity or similarity can be maximized by aligning the compared sequences alongside each other, sliding them back and forth, and conservatively introducing gaps in the sequences where necessary. The percent identity is calculated by counting the number of identical aligning residues dividing by the total length of the aligned region, including gaps in both sequences, and multiplying by 100. Identity would thus be expressed as, e.g., "60% identity over 200 amino acids," or "57% identity over 250 amino acids." Similarity is calculated by counting both identities and similarities in the above calculation. For example, the alignment below (SEQ ID NOs:14 and 15, has 37.5% sequence identity over 56 amino acids ((21 identities/56 residues)×100% ), where 56 is the total length of the aligned region.

The invention further encompasses polynucleotides which code for the above-described polypeptides of the present invention. These polynucleotides may be in the form of RNA or in the form of DNA, which DNA includes cDNA, genomic DNA, and synthetic DNA. The DNA may be double-stranded or single-stranded. The polynucleotides may include: only the coding sequence for the mature polypeptide; the coding sequence for the mature polypeptide and additional coding sequence such as a leader or secretory sequence or a proprotein sequence; the coding sequence for the mature polypeptide (and, optionally, additional coding sequence) and non-coding sequence, such as introns or non-coding sequence 5' and/or 3' of the coding sequence for the mature polypeptide. Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the herein above-described polynucleotides. The variants of the polynucleotides may be naturally occurring allelic variants of the polynucleotides or non-naturally occurring variants of the polynucleotides. As known in the art, an allelic variant is an alternate form of a polynucleotide sequence which may have a substitution, deletion, or addition of one or more nucleotides which does not substantially alter the function of the encoded polypeptides. Thus, the present invention includes polynucleotides encoding the same mature polypeptide as described in Example 1, below, as well as variants of such polynucleotides which variants include deletion variants, substitution variants and addition or insertion-variants.

The present invention also includes polynucleotides wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide

```
RTPSDKPVAH--VANPQLQWLNRRANALLANGVE-RDNQLVV--EGLYLIYSQVLF   56 resid.
|  |   |    ||   |||        |  ||   |  ||     |||  |   |   21 ident.
RAPFKKSWAYLQVAKHKLSW-NK--DGIL-HGVRYQDGNLVIQFPGLYFIICQLQF   56 resid.
```

As a further example, the same alignment below (SEQ ID NOs:14 and 15) has 55.4% sequence similarity over 56 amino acids ((31 similarities/56 residues)×100% ), where 56 is the total length of the aligned region. In this example, conservative substitutions are indicated by a plus sign and the total similarities is given by the sum of the identities and the conservative substitutions. (As noted above, determination of conservative substitutions is dependent on the scoring matrix chosen. The same alignment below may yield a different value for percent similarity using a different scoring matrix.)

having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. For example, the polynucleotides of the present invention may code for a mature protein or for a protein having a prosequence or for a protein having both a prosequence and a presequence (leader sequence).

```
RTPSDKPVAH--VANPQLQWLNRRANALLANGVE-RDNQLVVE--GLYLIYSQVLF   56 resid.
R P  K  A+   VA  +L W N+   +  +L +GV  +D   LV++  GLY I  Q+ F   31 simil.
RAPFKKSWAYLQVAKHKLSW-NK--DGIL-HGVRYQDGNLVIQFPGLYFIICQLQF   56 resid.
```

Both of the sequences in the aligned region may be contained within longer, less homologous sequences. "Unrelated" or "non-homologous" sequences typically share less than 40% identity at the peptide level, preferably less than 25% identity.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (69).

The term "gene" means the segment of DNA involved in producing a polypeptide chain; it includes regions preceding and following the coding region (leader and trailer) as well as intervening sequences (introns) between individual coding segments (exons). Fragments of the full length BTL.009 gene may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete BTL.009 gene including regulatory and promotor regions, exons, and introns. An example of a screen comprises isolating the coding region of the BTL.009 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention is directed to polynucleotides having at least a 70% identity, preferably at least 90% identity, and more preferably at least a 95% identity to a polynucleotide which encodes a polypeptide of the present invention, as well as fragments thereof, which fragments have at least 30 bases and preferably at least 50 bases and to polypeptides encoded by such polynucleotides.

The present invention also relates to vectors that include polynucleotides of the present invention as above described, host cells that are genetically engineered with vectors of the invention, and the production of polypeptides of the invention by recombinant techniques. Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amphlifying the BTL.009 genes. The culture conditions, such as temperature, pH and the like, are those previously used with the host cell selected for expression, and will be apparent to the ordinarily skilled artisan. The polynucleotide of the present invention may be employed for producing a polypeptide by recombinant techniques.

Thus, for example, the polynucleotide sequence may be included in any one of a variety of expression vehicles, in particular vectors or plasmids for expressing a polypeptide. Such vectors include chromosomal, non-chromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. Such procedures and others are deemed to be within the scope of those skilled in the art. The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda PL promoter and other promoters known to control expression of genes in prokaryotic or eukaryotic cells or their viruses. The expression vector may also contain a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli. The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as E. coli, Salmonella typhimurium, Streptomyces; fungal cells, such as yeast; insect cells, such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available. The following vectors are provided by way of example. Bacterial: pQE70, pQE60, pQE-9 (Qiagen), pBS, phagescript, psiX174, pBluescript SK, pBsKS, pNH8a, pNH16a, pNH18a, pNH46a (Stratagene), pTRC99A, pKK223-3, pKK233-3, pDR540, PRIT5 (Pharmacia). Eukaryotic: pWLneo, pSV2cat, pOG44, pXT1, pSG (Stratagene) pSVK3, pBPV, pMSG, PSVL (Pharmacia). However, any other plasmid or vector may be used as long as they are viable in the host. Promoter regions can be selected from any desired gene using CAT (chloramphenicol acetyl transferase) vectors or other vectors with selectable markers. Two appropriate vectors are pKK232-8 and pCM7. Particular named bacterial promoters include laci, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention also relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (70). The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook (71), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually from about 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers. Generally, recombinant expression vectors will include origins of replication and selectable markers permitting transformation of the host cell, e.g., the ampicillin resistance gene of $E.\ coli$ and $S.\ cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation, initiation, and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include $E.\ coli,\ Bacillus\ subtilis,\ Salmonella\ typhimurium$ and various species within the genera Pseudomonas, Streptomyces, and Staphylococcus, although others may also be employed as a matter of choice. Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis.) These pBR322 "backbone" sections are combined with an appropriate promoter and the structural sequence to be expressed.

After transformation of a suitable host strain and growth of the host strain to an appropriate cell density, the selected promoter may be de-repressed, if necessary, by appropriate means (e.g., temperature shift or chemical induction) and the cells may be cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts (82) and other cell lines capable of expressing a compatible vector, for example, the C127, 3T3, CHO, HeLa and BHK cell lines. Mammalian expression vectors will generally comprise an origin of replication, a suitable promoter and enhancer, and also any necessary ribosome binding sites, polyadenylation site, splice donor and acceptor sites, transcription termination sequences, and 5' flanking nontranscribed sequences. DNA sequences derived from the SV40 viral genome, for example, SV40 origin, early promoter, enhancer, splice, and polyadenylation sites may be used to provide the required non-transcribed genetic elements.

The polypeptide of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptide of the present invention may be a naturally purified product, or a product of chemical synthetic-procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

EXAMPLE 1

Production of BTL.009

Materials

Bovine chymotrypsin and Tos-Gly-Pro-Arg-7-amido-4-methylcoumarin (Tos-GPR-AMC) were from Sigma (St. Louis, Mo.). Human neutrophil elastase, Cathepsin G, and Proteinase 3 were purchased from Athens Research and Technology, Inc. (Athens, Ga.). Suc-AAPF-AMC, and Suc-AAPV-AMC were from Bachem Bioscience (King of Prussia, Pa.).

Synthesis and Refolding of EST-Derived Kunitz Domain

A peptide (BTL.009) corresponding to the Kunitz domain (KQDVCEMPKETGPCLAYFLHWWYDKKDNTCSMF-VYGGCQGNNNNFQSKANCLNTC (SEQ ID NO:1)) identified within the sequence of the EST-derived putative protein was synthesized by Genosys Biotechnologies Inc. (The Woodlands, Tex.). The synthetic peptide was refolded to yield the functional domain using an adaptation of the method of Tam et al. (83) as follows. A solution containing 23% (v/v) dimethyl sulfoxide in 0.1 M Tris-HCl (pH 6.0) was added dropwise to a solution of reduced peptide (3.4 mg/ml) in 0.1 M Tris-HCl (pH 6.0) containing 8M urea to obtain a final concentration of 0.3 mg/ml peptide in 20% dimethyl sulfoxide, 0.1 M Tris-HCl (pH 6.0), and 1 M urea. The solution was stirred at 25° C. for 24 hours. Refolded material was applied to a Vydac C8 reverse phase column (5 μm, 0.46×25 cm) and washed with 20% acetonitrile in 0.1% trifluoroacetic acid (TFA) and eluted using a 40 minute linear gradient of 20–50% acetonitrile in 0.1% TFA at a flow rate of 1 ml/min. Fractions containing chymotrypsin inhibitory activity (see below) were pooled, lyophilized, dissolved in 0.1% TFA, and stored at −20° C. until needed.

Chymotrypsin Assay to Monitor Protein Folding

To identify the properly folded form from reverse phase purification, the inhibition of chymotrypsin was measured. Chymotrypsin (20 nM) was incubated with refolded BTL.009 reverse phase fractions (0.04 absorbance units at 280 nm) in 100 μl of 50 MM Hepes (pH 7.5), 0.15 M NaCl, 2.0 mM $CaCl_2$, and 0.01% Triton X-100 (buffer A) at 37° C. After 30 minutes, Suc-AAPF-pNa (100 μM final concentration) was added, after which the residual enzymatic formation of pNa was monitored at 410 nm.

Determination of Equilibrium Dissociation Constants

Apparent equilibrium dissociation constants (Ki*) were determined as described previously (44) assuming enzyme:inhibit or stoichiometries of 1:1. The BTL.009 concentration was determined by amino acid analysis. The concentration of human neutrophil elastase, cathepsin G, and proteinase 3 were based on the manufacturer's specifications. Following preincubation of protease with inhibitor for 30 minutes at 37° C. in 1 ml of buffer A, reactions were initiated with substrate to achieve the following initial component concentrations: hum an neutrophil elastase with [Eo]=120 pM and 200 μM Suc-AAPV-AMC (Km=450 μM); human neutrophil cathepsin G with [Eo]=9.3 nM and 500 μM Suc-AAPF-AMC; human neutrophil proteinase 3 with [Eo]=72 nM and 530 μM Suc-AAPV-AMC (Km=600 μM). Hydrolysis of AMC-conjugated peptides was monitored on a Hitachi model F4500 fluorometer (excitation=370 nm, emission=432 nm) over the first 2 minutes of the reaction. Ki* values were determined from plots of fractional rate versus inhibitor concentration, which were fit by nonlinear regression analysis (Enzifitter™ by Bio soft, Cambridge UK) as described (44). Ki values were obtained by correction for the effect of substrate as described (44).

Results

The synthetic peptide containing the Kunitz domain (BTL.009) was prepared as described above. The purified reduced peptide gave a mass number of [M-H]+=6,347 as determined by mass spectrometric analysis and contained the expected amino acid composition. Refolding of the peptide using dimethylsulfoxide as the oxidizing agent followed by purification on a C8 column yielded purified refolded BTL.009 (1.5% of the starting material) which exhibited a [M-H]+ value of 6,341. The mass reduction upon refolding (6 mass units) suggests that the refolding had resulted in the formation of three intrachain disulfide bonds from the six cysteines present within the reduced peptide.

As shown below, the BTL.009 protein contains the same pattern of six conserved cysteine residues shared by the Kunitz domains of the other members of the Kunitz domain family of proteinase inhibitors.

| SEQ ID# | protein | sequence of Kunitz domain | | |
|---|---|---|---|---|
| 2 | Aprotinin | RPDFCLEPPY | TGPCKARIIR | YFYNAKAGLC | 30 |
| 3 | APP | VREVCSEQAE | TGPCRAMISR | WYFDVTEGKC | 30 |
| 4 | coll a-3 | ETDICKLPKD | EGTCRDFILK | WYYDPNTKSC | 30 |
| 5 | TFPI-KD1 | MHSFCAFKAD | DGPCKAIMKR | FFFNIFTRQC | 30 |
| 6 | TFPI-KD2 | KPDRCFLEED | PGICRGYITR | YFYNNQTKQC | 30 |

-continued

| SEQ ID# | protein | sequence of Kunitz domain | | |
|---|---|---|---|---|
| 7 | TFPI-KD3 | GPSWCLTPAD | RGLCRANENR | FYYNSVIGKC | 30 |
| 1 | BTL.009 consensus | KQDVCEMPKE C | TGPCLAYFLH C | WWYDKKDNTC C | 30 |
| 2 | Aprotinin | QTFVYGGCRA | KRNNFKSAED | CMRTCGGA | 58 |
| 3 | APP | APFFYGGCGG | NRNNFDTEEY | CMAVC | 55 |
| 4 | coll a-3 | ARFWYGGCGG | NENKFGSQKE | CEKVCAPV | 58 |
| 5 | TFPI-KD1 | EEFIYGGCEG | NQNRFESLEE | CKKMCTRD | 58 |
| 6 | TFPI-KD2 | ERFKYGGCLG | NMNNFETLEE | CKNIC | 55 |
| 7 | TFPI-KD3 | RPFKYSGCGG | NENNFTSKQE | CLRACKKG | 58 |
| 1 | BTL.009 consensus | SMFVYGGCQG C | NNNNFQSKAN | CLNTCKNK C C | 58 |

(APP = Alzheimer's beta-amyloid Precursor Protein; coll = collagen; TFPI-KD = Tissue Factor Pathway Inhibitor-Kunitz Domain)

The P1 residue in BTL.009 is a leucine, a large hydrophobic residue with an aliphatic side chain. Therefore, BTL.009 is predicted to have a unique specificity profile that falls somewhere between the specificity profiles of elastase-like proteinases and chymotrypsin-like proteinases that selectively cleave at hydrophobic residues with large aromatic side chains. Thus, the potency of the refolded Kunitz domain against the human neutrophil proteinases leukocyte elastase, cathepsin G, and proteinase 3 was investigated. Results indicate that BTL.009 is a strong inhibitor of leukocyte elastase, a moderate inhibitor of proteinase 3, and a weak inhibitor of cathepsin G. See the Table.

TABLE

Interaction of BTL. 009 with human neutrophil proteinases

| Protease | Ki † |
|---|---|
| Leukocyte elastase | 8.0 |
| Cathepsin G | 1,800 |
| Proteinase 3 | 190 |

†Equilibrium dissociation constants (Ki values) are listed in nM.

The present invention, BTL.009, is the first natural serine proteinase inhibitor of the Kunitz family to be described that exhibits significantly greater inhibitory activity towards a neutral serine proteinase secreted by neutrophils than towards trypsin. As all known serine proteinase inhibitors that exhibit poor activity towards trypsin are also poor inhibitors of other serine proteinases that share the same P1 specificity of trypsin (i.e., arginine or lysine), it is expected that BTL.009 will have little activity towards all trypsin-like proteinases. In addition, as trypsin-like serine proteinases are known to play important roles in many physiological processes such as blood coagulation and fibrinolysis, the narrow specificity of BTL.009 towards leukocyte elastase should result in fewer undesirable proteolytic effects during treatment with this protein.

EXAMPLE 2

BTL.009 exhibits greater potency towards leukocyte elastase (Ki=8 nM) than any other described natural serine proteinase inhibitor of the Kunitz family. However, BTL.009 exhibits poorer activity towards the other two activated neutrophil-derived serine proteinases, proteinase 3 (190 nM) and cathepsin G (Ki=1800 nM). Increased activity of BTL.009 towards other proteinases may be obtained through production of BTL.009 variants via mutagenesis of the protein structure at the P1 residue (Leu15) and other residues corresponding to contact sites with target proteinases (residues 11–14, 16–19 and 34–39). The binding specificities of numerous serine proteinase inhibitors of the Kunitz and other families have been altered through replacement of key binding residues via semisynthetic means and mutagenesis.

Aprotinin variants containing a mutation at the P1 site produced by mutagenesis and displayed on bacteriophage M13 [Lys15>Leu] or produced through semisynthesis [Lys15>Val] exhibited greatly enhanced inhibitory activity towards leukocyte elastase (Ki=2.9 nM and Ki=0.11 nM, respectively) (72–73). Both aprotinin variants were inactive towards trypsin. The P'2 position of aprotinin was also demonstrated to be important in determining binding specificity. Aprotinin variants produced in *Escherichia coli* with positions P1 and P'2 positions substituted with the hydrophobic amino acids phenylalanine, tyrosine, and leucine acted specifically against chymotrypsin-like proteinases (74). Some of the variants, particularly those with phenylalanine or leucine substitutions, also exhibited inhibitory activity against cathepsin G (Ki~10 nM). Aprotinin variants containing single mutations have not exhibited inhibitory activity towards cathepsin G.

Substitution of the putative P1 residue, arginine, with valine in Alzheimer's beta-amyloid precursor protein Kunitz domain (APP KD) by site-directed mutagenesis eliminated the ability of the protein to inhibit its usual substrates, trypsin, factor Xia, and chymotrypsin (84). Instead, the APP KD variant was a potent inhibitor of leukocyte elastase (Ki=0.8 nM), for which the wild-type inhibitor exhibits no activity.

Phage display systems have also been used to alter the specificity of APP KD. Alterations at or near the binding loop (positions 11–13, 15–19 and 34) and construction of consensus mutants by site directed mutagenesis resulted in a very potent plasma kallikrein APP KD variant inhibitor (Ki~0.015 nM) that differed from APP KD at 6 key residues (T11D, P13H, M17A, I18H, S19P and F34Y) (75). This APP KD variant had an increase in binding affinity to plasma kallikrein of more than 10,000-fold compared to wild-type APP KD. Phage display involving alterations in the primary and secondary binding loops was also employed to convert APP KD into potent inhibitors of tissue factor-Factor VIIa complex (TF•FVIIa) (75). The most striking difference in the selected Kunitz domain sequences was determined to be at the P4' position where Lys was highly preferred. APP KD variants that exhibited high potency towards TF•FVIIa were obtained (Ki=2 to 20 nM); the Ki values for these variants were generally >1 $\mu$M for FXIa and plasma kallikrein and ranged from 4 to 200 nM for plasmin.

The Kunitz domain 1 of human lipoprotein-associated coagulation inhibitor was displayed on the III protein of phage M13, and libraries of the Kunitz domain were made (76). Residues corresponding to the P1 region (positions 10–21) and the "second loop" (positions 31–39) were iteratively varied, and the resulting phage libraries were selected for binding to the serine proteinases plasmin and plasma kallikrein (63). Highly potent specific inhibitors of both proteinases (Ki=0.04–0.08 nM) were identified with this iterative strategy.

Alpha 1-proteinase inhibitor, a serpin family serine proteinase inhibitor, is a potent inhibitor of leukocyte elastase and cathepsin G (22, 77). Substitution of the P1 residue, Met358 with an alanine, isoleucine or valine by site-directed mutagenesis resulted in efficient inhibitors of leukocyte and pancreatic elastase but not of cathepsin G. The alpha 1-proteinase inhibitor [Phe358] variant was a potent specific inhibitor of cathepsin G whereas the alpha 1-proteinase inhibitor [Arg358] variant was a potent inhibitor of trypsin-like molecules such as thrombin but not of leukocyte elastase (78). The P3 site of alpha 1-proteinase inhibitor (position 356) was also determined to be important in conferring specificity as alpha 1-proteinase inhibitor [Ala356, Val358] inhibited pancreatic elastase but not leukocyte elastase (22). Oxidation of Met358 in alpha 1-proteinase inhibitor results in a loss of inhibitor activity. The alpha 1-proteinase variants containing alanine, valine, isoleucine and leucine in the P1 site were all resistant to oxidation, and the most active variant, alpha 1-proteinase inhibitor [Leu358], was proposed as a potential therapeutic for the therapy of destructive lung disorders. Similarly, alpha 1-proteinase inhibitor [Arg358] was proposed to be effective in the control of thrombosis.

Human secretory trypsin inhibitor (hPSTI), a member of the Kazal serine proteinase family, is a potent inhibitor of trypsin and is completely inactive towards chymotrypsin- and elastase-like porteinases. Substitution of the P1 residue lysine with leucine in HPSTI by site-directed mutagenesis resulted in a variant that was inactive towards trypsin but highly potent towards leukocyte elastase (Ki=0.025 nM) and somewhat less active towards chymotrypsin (Ki=8 nM) (79). Introduction of a second mutation in the single mutant hPSTI variant, a substitution of isoleucine with glutamate at the P'1 site, resulted in a nearly equipotent inhibitor of chymotrypsin (Ki=0.024 nM) and leukocyte elastase (Ki=0.037 nM). Replacement of leucine with a tyrosine at the P1 site in the double mutant hPSTI variant resulted in a potent inhibitor of chymotrypsin (Ki=0.016 nM) but a significantly weaker inhibitor of leukocyte elastase (Ki>10 $\mu$M).

Phage display systems and site-directed mutagenesis can be used to identify BTL.009 variants with increased potency towards leukocyte elastase or altered and improved specificities towards other targeted proteinases such as cathepsin G and proteinase 3. BTL.009 can be displayed on the III or VI protein of phage M13, and libraries of the BTL.009 kunitz domain can be made (76, 80). Highly potent inhibitors towards targeted proteinases can be identified through the iterative construction of BTL.009 variants with mutations at the P1 residue and surrounding residues that contact the inhibited proteinases (residues Thr11-Pro13, Leu15-Leu19, Val34-Gly37 and Gln39) and selection through binding to the targeted proteinases (80). Further selection of high binding BTL.009 variants can be made through the construction of "consensus muteins" via site-specific mutagenesis.

As proteinase 3 has a specificity preference of small aliphatic side chains (e.g., Ala, Ser, Val), increased potency of BTL.009 towards proteinase 3 may be obtained through substitution of the P1 residue, Leu15, in BTL.009 with a small aliphatic amino acid. Increased potency of BTL.009 towards leukocyte elastase and cathepsin G may also result from substitution of the P1 Leu residue to alternate favored amino acids such as Val, Ala, and Ile (leukocyte elastase) and Phe, Arg, and Lys (cathepsin G). Substitution of the P1 residue with an arginine or lysine would also be expected to significantly increase the potency of BTL.009 towards trypsin-like proteinases.

Increased potency of BTL.009 towards proteinases may also be effected through changes at sites other than the P1 residue (Leu15). For example, substitution of the P'2 residue, Tyr17, with a Phe or Leu may result in a more potent cathepsin G inhibitor (74). Increased potency of BTL.009 variants towards elastase, cathepsin G, proteinase 3 and other serine proteinases may be further constructed through the iterative mutagenesis of BTL.009 within positions 11–13, 14–19, 34–37 and 39 as described above. The BTL.009 variants with altered potencies towards proteinases would preferably have at least 76% identity over 55 residues to BTL.009, more preferably at least 89% identity over 55 residues to BTL.009.

Conclusion

The above examples are intended to illustrate the invention and it is thought variations will occur to those skilled in the art. Accordingly, it is intended that the scope of the invention should be limited only by the claims below.

References

1. Watorek et al., Adv Exp Med Biol 1988;240:23–31
2. Murata et al., Inflammation August 1994;18(4):337–47
3. Yavin and Fridkin, J Pept Res April 1998;51(4):282–9
4. Higuchi et al., Blood Apr. 1, 1992;79(7):1712–9
5. Fritz, H., Ciba Found Symp 1979;(75):351–79
6. Swaim and Pizzo. Biochem J Aug. 15, 1988;254(1):171–8
7. Morishita et al., Thromb Res Feb. 15, 1994;73(3–4):193–204
8. Frenkel, K., et al., Carcinogenesis 1987;8(9):1207–12
9. Chopin et al., Eur J Biochem Nov. 1, 1997;249(3):733–8
10. Lomas et al., J Biol Chem Oct. 6, 1995;270(40):23437–43
11. Hazuda et al., J Biol Chem Apr. 15, 1990;265(11):6318–22
12. Mrowietz et al., J Invest Dermatol September 1991;97(3):529–33
13. Palmgren et al., J Allergy Clin Immunol April 1992;89(4):905–15
14. Ferry et al., FEBS Lett Feb. 3, 1997;402(2–3):111–5
15. Rao et al., J Biol Chem May 25, 1991;266(15):9540–8
16. Kao, R. C., et al., (1988) J. Clin. Invest. 82, 1963–1973
17. Senior, R. M., et al., Am Rev Respir Dis September 1977;116(3):469–75
18. Schnebli et al., Eur J Respir Dis Suppl 1985;139:66–70
19. Uejima et al., J Pharmacol Exp Ther May 1993;265(2):516–23
20. Doring G. Am J Respir Crit Care Med December 1994;150(6 Pt 2):S114–7
21. Smith et al., FEBS Lett Jul. 22, 1996;390(2):187–90
22. Jallat et al., Rev Fr Transfus Immunohematol September 1986;29(4):287–98
23. Selak M A. Thromb Haemost Nov. 10, 1992;68(5):570–6
24. Hogg et al., J Biol Chem Oct. 15, 1993;268(29):21811–8
25. Fagny et al., Regul Pept Nov. 20, 1992;42(1–2):27–37
26. Wintroub et al., Biochemistry Jan. 17, 1984;23(2):227–32
27. Tonnesen et al., J Clin Invest 1982, 69(1):25–30
28. Lu W et al., J. Mol. Biol. Feb. 21, 1997;266(2):441–61
29. Stein R. Arch. Biochem. Biophys. Feb. 1, 1985;236(2):677–680
30. Polanowska et al., Biochim Biophys Acta Jul. 28, 1998;1386(1):189–98
31. Brubaker et al., Biochem Biophys Res Commun Nov. 16, 1992; 188(3):1318–24
32. Stein et al., Biochemistry Mar. 10, 1987;26(5):1301–5
33. Laskowski, M. et al., 1980, Ann. Rev. Biochem. 49:593–626
34. Roberts, L. et al., 1992, PNAS 89:2429–33
35. Davis, R. & Whittington, R., 1995, Drugs 49:954–983
36. Meissauer, A. et al., 1991, Exp. Cell Res. 192:453–9
37. Greenwood, J., 1991, Neuroradiology 33:95–100
38. Coleman, 1984, J. Clin. Invest. 73:1249
39. Vallet et al., Nature 389:607
40. Chraibi et al., J. Gen. Physiol., 111:127
41. Huang, Y. et al., 1998, J. Leukoc. Biol. 64: 322–30
42. Dela Cadena, R. et al., 1995, FASEB J. 9:446–452
43. Laurenti et al., 1996, Diabetic Medicine 13:642–645
44. Delaria et al., 1997, J. Biol. Chem. 272:12209–12
45. Petersen et al., Eur J Biochem Jan. 15, 1996;235(1–2):310–6
46. Petersen et al., Thromb Haemost May 4, 1992;67(5):537–41
47. Johnson et al., Thromb Haemost October 1998;80(4):585–7
48. Nakamura et al., J Biochem (Tokyo) May 1987;101(5): 1297–306
49. Bosterling and Quast, Biochim Biophys Acta Jan. 15, 1981;657(1):58–72
50. Morris and Sakanari, J Biol Chem Nov. 4, 1994;269(44):27650–6
51. Valueva et al., Biochemistry (Mosc) 1997 62(12):1367–74
52. Mallory and Travis, Am J Clin Nutr August 1975;28(8):823–30
53. Duranton et al., Biochemistry Aug. 11, 1998;37(32):11239–45
54. Gardi et. al, G. Biochem J Apr. 1, 1994;299 (Pt 1):237–45
55. Reilly and Travis, Biochim Biophys Acta Jan. 24, 1980;621(1): 147–57
56. Frost et al., Int J Biochem Cell Biol April 1997;29(4):595–603
57. Sugimori et al., Am J Respir Cell Mol Biol September 1995;13(3):314–22
58. Wiedow et al., J Biol Chem Sep. 5, 1990;265(25):14791–5
59. Boudier et al., Adv Exp Med Biol 1988; 240: 115–22
60. Fukusen et al., Biochem Med Metab Biol October 1987;38(2):165–9
61. Faller et al., Biochem J Sep. 15, 1990;270(3):639–44
62. Seemuller et al., Hoppe Seylers Z Physiol Chem December 1980;361(12):1841–6
63. T. E. Creighton, Proteins Structure and Molecular Properties, 2nd Ed., W.H. Freeman and Co., New York (1993)
64. B. C. Johnson, Ed., Posttranslational Covalent Modification of Proteins, Academic Press, New York, pp. 1–12 (1983)
65. Seifter et al., 1990, Meth Enzymol 182: 626–646
66. Rattan et al., 1992, Ann N.Y. Acad Sci 663: 48–62
67. Dayhoff, The Atlas of Protein Sequence and Structure 5 (1978)
68. Argos, EMBO J. 8: 779–785 (1989)
69. Wilson et al., 1984, Cell 37: 767
70. Davis et al., Basic Methods in Molecular Biology, (1986)
71. Sambrook, et al., Molecular Cloning: A Laboratory Manual, 2d Ed., (Cold Spring Harbor, N.Y., 1989)
72. Roberts et al., Gene Nov. 2, 1992;121(1):9–15
73. Beckmann et al., Eur J Biochem Oct. 1, 1988; 176(3): 675–82
74. Brinkmann et al., Eur J Biochem Nov. 15, 1991;202(1):95–9

75. Dennis and Lazarus. J Biol Chem Sep. 2, 1994;269(35):22137–44
76. Ley et al., Mol Divers October 1996;2(1–2):119–24
77. Jallat et al., Protein Eng October–November 1986;1(1):29–35
78. Travis et al., Biol Chem Hoppe Seyler September 1986;367(9):853–9
79. Collins et al., Biol Chem Hoppe Seyler May 1990;371 Suppl:29–36
80. Jespers et al., Biotechnology (N Y) April 1995;13(4):378–82
81. Starkey P M., Acta Biol Med Ger 1977;36(11–12):1549–54
82. Gluzman, 1981, Cell 23: 175
83. Tam et. al. (1991) J. Am. Chem. Soc. 113, 6657–62
84. Sinha et. al. J Biol Chem Nov. 5, 1991;266(31):21011–3
85. Sprecher et al., U.S. Pat. No. 5,914,315 (Jun. 22, 1999).

What is claimed is:

1. An isolated protein characterized by having a deduced amino acid sequence of SEQ ID NO:1.

2. The protein according to claim 1 having protease inhibitory activity, wherein the protein inhibits at least one protease selected from the group consisting of leukocyte elastase, cathepsin G, proteinase 3, and α-chymotrypsin.

3. The protein according to claim 2, wherein the protease inhibited is leukocyte elastase.

4. A mutant protein having protease inhibitory activity, wherein the protein inhibits at least one protease selected from the group consisting of leukocyte elastase, cathepsin G, proteinase 3, and α-chymotrypsin, and having a deduced amino acid sequence that differs from SEQ ID NO:1 in at least one position selected from the group consisting of position 11, position 12, position 13, position 15, position 16, position 17, position 18, position 19, position 34, position 35, position 36, position 37, and position 39.

5. The protein according to claim 4, the protein further described as having one or more amino acid substitutions selected from the group consisting of (a) threonine at position 11 substituted with aspartate, glutamate, proline, or arginine;

(b) proline at position 13 substituted with alanine, leucine, isoleucine, threonine, or histidine;

(c) leucine at position 15 substituted with methionine, lysine, arginine, alanine, serine, isoleucine, valine, phenylalanine, or tyrosine;

(d) alanine at position 16 substituted with glycine, isoleucine, aspartate, or glutamate;

(e) tyrosine at position 17 substituted with asparagine, arginine, isoleucine, alanine, methionine, valine, phenylalanine, or leucine;

(f) phenylalanine at position 18 substituted with methionine, glutamate, isoleucine or histidine;

(g) leucine at position 19 substituted with asparagine, threonine, lysine, serine or proline; and (h) valine at position 34 substituted with lysine, isoleucine, tryptophan, phenylalanine or tyrosine.

6. A pharmaceutical composition for inhibiting protease activity comprising a protein according to claim 1 and a pharmaceutically acceptable carrier.

* * * * *